United States Patent
Cho

(10) Patent No.: US 11,047,832 B2
(45) Date of Patent: Jun. 29, 2021

(54) METHOD AND SYSTEM FOR DETERMINING AT LEAST ONE PARAMETER OF INTEREST OF A MATERIAL

(71) Applicant: ENDRA Life Sciences Inc., Ann Arbor, MI (US)

(72) Inventor: Jang Hwan Cho, Ann Arbor, MI (US)

(73) Assignee: ENDRA Life Sciences Inc., Ann Arbor, MI (US)

(*) Notice: Subject to any disclaimer, the term of this patent is extended or adjusted under 35 U.S.C. 154(b) by 209 days.

(21) Appl. No.: 16/554,682

(22) Filed: Aug. 29, 2019

(65) Prior Publication Data

US 2021/0063356 A1   Mar. 4, 2021

(51) Int. Cl.
*G01N 29/24* (2006.01)
*G01N 29/44* (2006.01)
*G01N 33/50* (2006.01)

(52) U.S. Cl.
CPC ......... *G01N 29/2431* (2013.01); *G01N 29/44* (2013.01); *G01N 33/5067* (2013.01); *G01N 2291/02881* (2013.01)

(58) Field of Classification Search
CPC .............. G01N 29/2431; G01N 29/44; G01N 29/0654; G01N 2291/02881; G01N 2291/02863; G01N 33/5067; G01N 33/483; G01N 2291/106
See application file for complete search history.

(56) References Cited

U.S. PATENT DOCUMENTS

| | | | |
|---|---|---|---|
| 9,888,879 B1* | 2/2018 | Cho | A61B 5/0095 |
| 9,888,880 B1 | 2/2018 | Cho et al. | |
| 9,980,677 B1 | 5/2018 | Cho et al. | |
| 2002/0079121 A1* | 6/2002 | Ryan | B29C 66/472 174/68.1 |
| 2008/0288028 A1* | 11/2008 | Larson | H04B 1/0458 607/60 |

OTHER PUBLICATIONS

Blaine R. Copenheaver; PCT International Search Report and Written Opinion; dated Nov. 19, 2020; 10 pages total; WIPO; Alexandria, VA, United States.

* cited by examiner

*Primary Examiner* — Suman K Nath
(74) *Attorney, Agent, or Firm* — Stanley E. Jelic

(57) ABSTRACT

A method for determining at least one parameter of interest of a material comprises directing, using a radio frequency (RF) applicator, one or more RF energy pulses into a region of interest, the region of interest comprising a material having a parameter of interest and at least one reference, the material and the reference separated by at least one boundary; detecting, using an acoustic receiver, at least one multi-polar acoustic signal generated in the region of interest in response to the RF energy pulses; processing the at least one multi-polar acoustic signal to determine an electric field strength at the boundary; calculating a voltage standing wave ratio (VSWR) of the one or more RF energy pulses; and determining the at least one parameter of interest of the material based at least on the determined electric field strength and the VSWR.

19 Claims, 8 Drawing Sheets

METHOD AND SYSTEM FOR DETERMINING AT LEAST ONE PARAMETER OF INTEREST OF A MATERIAL

FIELD

The subject disclosure relates to thermoacoustic imaging and in particular to a method and system for determining at least one parameter of interest of a material.

BACKGROUND

Materials can be identified or quantified by making one or more measurements of the material and as a result, if the type of material is unknown, identification or quantification methods can be performed to identify the material. These methods often require the use of specialized equipment. For example, dielectric measurement systems require a specialized probe and network analyzer.

In medical settings such as in a hospital, this specialized equipment may not be readily available. As will be appreciate, if required, it is desirable to determine at least one parameter of a material using equipment that is readily available in a medical setting.

Although techniques for determining at least one parameter of interest of a material have been considered, improvements are desired. It is therefore an object at least to provide a novel method and system for determining at least one parameter of interest of a material.

SUMMARY

It should be appreciated that this summary is provided to introduce a selection of concepts in a simplified form that are further described below in the detailed description. This summary is not intended to be used to limit the scope of the claimed subject matter.

Accordingly, in one aspect there is provided a method for determining at least one parameter of interest of a material, the method comprising directing, using a radio frequency (RF) applicator, one or more RF energy pulses into a region of interest, the region of interest comprising the material having the parameter of interest and at least one reference, the material and the reference separated by at least one boundary; detecting, using an acoustic receiver, at least one multi-polar acoustic signal generated in the region of interest in response to the RF energy pulses; processing the at least one multi-polar acoustic signal to determine an electric field strength at the boundary; calculating a voltage standing wave ratio (VSWR) of the one or more RF energy pulses; and determining the at least one parameter of interest of the material based at least on the determined electric field strength and the VSWR.

In one or more embodiments, the at least one parameter of interest is one of a Grüneisen Parameter of the material and a conductivity of the material.

In one or more embodiments, the at least one parameter of interest is a product of the Grüneisen Parameter of the material and the conductivity of the material.

In one or more embodiments, the at least one parameter of interest is a specific heat capacity of the material.

In one or more embodiments, an identity of the material is known.

In one or more embodiments, the determining comprises estimating the at least on parameter of interest.

In one or more embodiments, an identity of the material is unknown.

In one or more embodiments, the determining comprises looking up the at least one parameter of interest in a lookup table.

In one or more embodiments, the method further comprises monitoring a forward power and a reflected power of the one or more RF energy pulses to calculate the VSWR.

In one or more embodiments, the electric field strength is determined based on an input power of the RF applicator and an attenuation coefficient of the reference.

In one or more embodiments, the electric field strength is determined based on an estimated thickness of the reference and an attenuation coefficient of the reference.

In one or more embodiments, each multi-polar acoustic signal corresponds to a separate boundary location.

In one or more embodiments, detecting the at least one multi-polar acoustic signal is achieved using a thermoacoustic imaging system.

According to another aspect, there is provided a system for determining at least one parameter of interest of a material, the system comprising a thermoacoustic imaging system comprising a radio frequency (RF) applicator configured to emit RF energy pulses into the region of interest comprising a material having at least one parameter of interest and a reference, the material and the reference separated by at least one boundary, and an acoustic receiver configured to receive at least one multi-polar acoustic signal generated in the region of interest in response to the RF energy pulses; and one or more processors configured to: process multi-polar acoustic signals received by the acoustic receiver to determine an electric field strength at the boundary; calculate a voltage standing wave ratio (VSWR) of the one or more RF energy pulses; and determine the at least one parameter of interest of the material based at least on the determined electric field strength and the VSWR.

In one or more embodiments, the at least one parameter of interest is one of a Grüneisen Parameter of the material and a conductivity of the material.

In one or more embodiments, the at least one parameter of interest is a product of the Grüneisen Parameter of the material and a conductivity of the material.

In one or more embodiments, the at least one parameter of interest is a specific heat capacity of the material.

In one or more embodiments, the system comprises at least one power monitor configured to monitor a forward and reflected power of the RF energy pulses, and the one or more processors are configured to calculate the VSWR using the forward and reflected power of the RF energy pulses.

In one or more embodiments, the electric field strength is determined based on an input power of the RF applicator and an attenuation coefficient of the reference.

According to another aspect there is provided a non-transitory computer readable medium having stored thereon computer program code executable by one or more processors to process at least one multi-polar acoustic signal generated in a region of interest comprising a material having a parameter of interest and at least one reference, the material and the at least one reference separated by at least one boundary, to determine an electric field strength at the boundary; calculate a Voltage Standing Wave Ratio (VSWR) of RF energy pulses directed into the region of interest; and determine at least one parameter of interest of the material based at least on the determined electric field strength and the VSWR.

BRIEF DESCRIPTION OF THE DRAWINGS

Embodiments will now be described more fully with reference to the accompanying drawings in which.

DETAILED DESCRIPTION OF THE EMBODIMENTS

Figure 1:
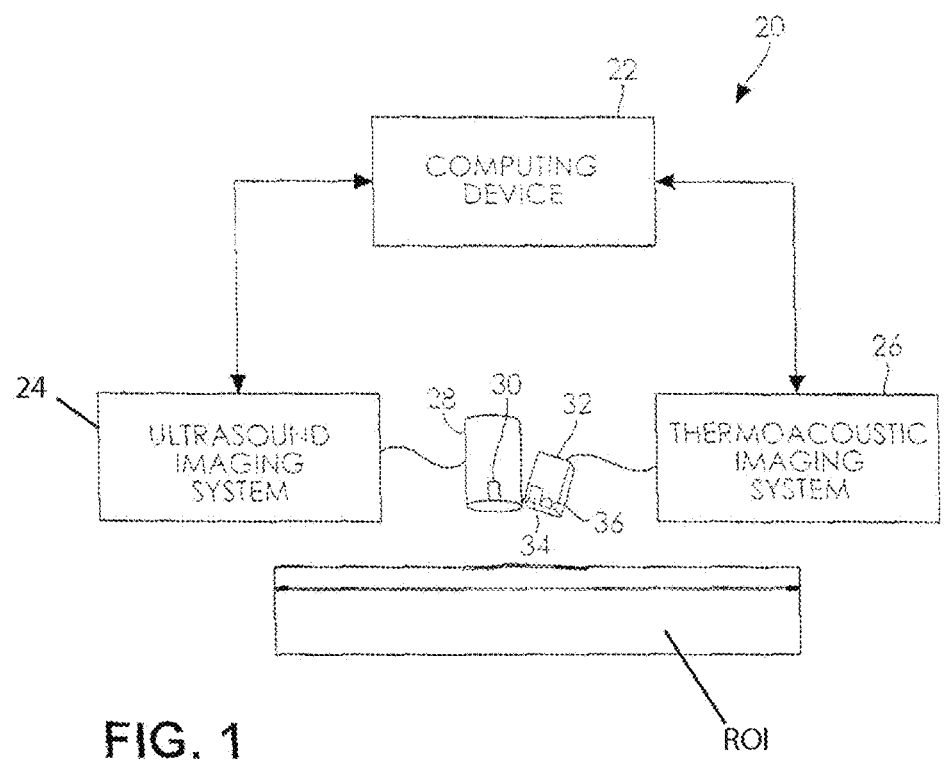
FIG. 1 is a schematic view of an imaging system wherein a region of interest is in vitro.

The foregoing summary, as well as the following detailed description of certain examples will be better understood when read in conjunction with the appended drawings. As used herein, an element or feature introduced in the singular and preceded by the word "a" or "an" should be understood as not necessarily excluding the plural of the elements or features. Further, references to "one example" or "one embodiment" are not intended to be interpreted as excluding the existence of additional examples or embodiments that also incorporate the described elements or features. Moreover, unless explicitly stated to the contrary, examples or embodiments "comprising" or "having" or "including" an element or feature or a plurality of elements or features having a particular property may include additional elements or features not having that property. Also, it will be appreciated that the terms "comprises", "has", "includes" means "including but not limited to" and the terms "comprising", "having" and "including" have equivalent meanings.

As used herein, the term "and/or" can include any and all combinations of one or more of the associated listed elements or features.

It will be understood that when an element or feature is referred to as being "on", "attached" to, "connected" to, "coupled" with, "contacting", etc. another element or feature, that element or feature can be directly on, attached to, connected to, coupled with or contacting the other element or feature or intervening elements may also be present. In contrast, when an element or feature is referred to as being, for example, "directly on", "directly attached" to, "directly connected" to, "directly coupled" with or "directly contacting" another element of feature, there are no intervening elements or features present.

It will be understood that spatially relative terms, such as "under", "below", "lower", "over", "above", "upper", "front", "back" and the like, may be used herein for ease of description to describe the relationship of an element or feature to another element or feature as illustrated in the figures. The spatially relative terms can however, encompass different orientations in use or operation in addition to the orientation depicted in the figures.

In the following, a method and system for determining at least one parameter of interest of a material are described. The method comprises directing, using a radio frequency (RF) applicator, one or more RF energy pulses into a region of interest, the region of interest comprising the material having the parameter of interest and at least one reference, the material and the reference separated by at least one boundary. An acoustic receiver is used to detect at least one multi-polar acoustic signal generated in the region of interest in response to the RF energy pulses. The at least one multi-polar signal is processed to determine an electric field strength at the boundary. A voltage standing wave ratio (VSWR) of the one or more RF energy pulses is calculated. The at least one parameter of interest is determined based at least on the determined electric field strength and the VSWR.

The at least one parameter of interest may be a Grüneisen Parameter of the material, a conductivity of the material, a product of the Grüneisen Parameter of the material and a conductivity of the material, salinity of a material, and/or a specific heat capacity of the material. Practical applications in a body can include estimating fat content in tissue and confirming whether a tumor is benign or malignant.

Turning now to FIG. 1, an exemplary imaging system is shown and is generally identified by reference numeral 20. As can be seen, the imaging system 20 comprises a programmed computing device 22 communicatively coupled to an ultrasound imaging system 24 and to a thermoacoustic imaging system 26. The ultrasound imaging system 24 and thermoacoustic imaging system 26 are configured to obtain ultrasound image data and thermoacoustic image data, respectively, of a region of interest ROI.

The programmed computing device 22 in this embodiment is a personal computer or other suitable processing device comprising, for example, a processing unit comprising one or more processors, system memory (volatile and/or non-volatile memory), other non-removable or removable memory (e.g., a hard disk drive, RAM, ROM, EEPROM, CD-ROM, DVD, flash memory, etc.) and a system bus coupling the various computer components to the processing unit. The computing device 22 may also comprise networking capabilities using Ethernet, Wi-Fi, and/or other suitable network format, to enable connection to shared or remote drives, one or more networked computers, or other networked devices. One or more input devices, such as a mouse and a keyboard (not shown) are coupled to the computing device 22 for receiving operator input. A display device (not shown), such as one or more computer screens or monitors, is coupled to the computing device 22 for displaying one or more generated images that are based on ultrasound image data received from the ultrasound imaging system 24 and/or the thermoacoustic image data received from thermoacoustic imaging system 26. The programmed computing device 22 executes program code stored on a computer readable medium and performs methods according to the program code as will be described in more detail below.

The ultrasound imaging system 24 comprises an acoustic receiver in the form of an ultrasound transducer 28 that houses one or more ultrasound transducer arrays 30 configured to emit sound waves into the region of interest ROI. Sound waves directed into the region of interest ROI echo off materials within the region of interest ROI, with different materials reflecting varying degrees of sound. Echoes that are received by the one or more ultrasound transducer arrays 30 of the ultrasound transducer 28 are processed by the ultrasound imaging system 24 before being communicated as ultrasound image data to the computing device 22 for further processing and for presentation on the display device as ultrasound images that can be interpreted by an operator. In this embodiment, the ultrasound imaging system 24 utilizes B-mode ultrasound imaging techniques assuming a nominal speed of sound of 1,540 m/s. As ultrasound imaging systems are known in the art, further specifics of the ultrasound imaging system 24 will not be described further herein.

The thermoacoustic imaging system 26 comprises an acoustic receiver in the form of a thermoacoustic transducer 32. The thermoacoustic transducer 32 houses one or more thermoacoustic transducer arrays 34 as well as a radio frequency (RF) applicator 36. It will however be appreciated that the RF applicator 36 may be housed separately from the thermoacoustic transducer 32. The RF applicator 36 is configured to emit short pulses of RF energy that are directed into materials within the region of interest ROI. In this embodiment, the RF applicator 36 has a frequency between about 10 Mhz and 100 GHz and has a pulse duration between about 0.1 nanoseconds and 10 nanoseconds. RF energy pulses delivered to materials within the region of interest ROI heat the materials thereby to induce acoustic pressure waves within the region of interest ROI that are detected by the thermoacoustic transducer 32. Acoustic pressure waves that are detected by the thermoacoustic transducer 32 are processed and communicated as thermoacoustic image data to the computing device 22 for further processing and for presentation on the display device as thermoacoustic images that can be interpreted by the operator.

In one potential embodiment, the ultrasound transducer 28 and thermoacoustic transducer 32 are mechanically interconnected so that the spatial relationship between the one or more ultrasound transducer arrays 30, the one or more thermoacoustic arrays 34 and the RF applicator 36 are known. The spatial relationship is set using a centerline of the one or more ultrasound transducer arrays 30, the one or more thermoacoustic transducer arrays 34, and RF applicator 36. The centerline of the ultrasound transducer array 34 and the thermoacoustic transducer array 34 is defined as being a mid-point of an area of the respective transduce array.

In this embodiment, the spatial relationship between the one or more ultrasound transducer arrays 30 and the one or more thermoacoustic transducer arrays 34 is such that the centerline of the one or more thermoacoustic transducer arrays 34 is set at a known angle α with respect to the centerline (also known as the axial axis or ultrasound transducer array beam axis) of the one or more ultrasound transducer arrays 30. The spatial relationship between the one or more thermoacoustic transducer arrays 34 and the RF applicator 36 is such that the centerline of the RF applicator 36 is spaced-apart and generally parallel to the centerline of the one or more thermoacoustic transducer arrays 34.

The imaging system 20 utilizes the known spatial relationship between the one or more ultrasound transducer arrays 30 and the one or more thermoacoustic transducer arrays 34 to increase the precision and accuracy of thermoacoustic imaging.

The coordinate system of the one or more ultrasound transducer arrays 30 of the ultrasound transducer 28 and the coordinate system of the one or more thermoacoustic transducer arrays 34 of the thermoacoustic transducer 32 are mapped by the computing device 22 so that acquired ultrasound and thermoacoustic images can be registered. Alternatively, the thermoacoustic imaging system 26 may make use of the one or more ultrasound transducer arrays 30 of the ultrasound transducer 28 by disconnecting the one or more ultrasound transducer arrays 30 from the ultrasound transducer 28 and connecting the one or more ultrasound transducer arrays 30 to the thermoacoustic transducer 32. As will be appreciated, by doing this coordinate mapping between the one or more ultrasound transducer arrays 28 and the one or more thermoacoustic transducer arrays 34 is not required.

Figure 2:
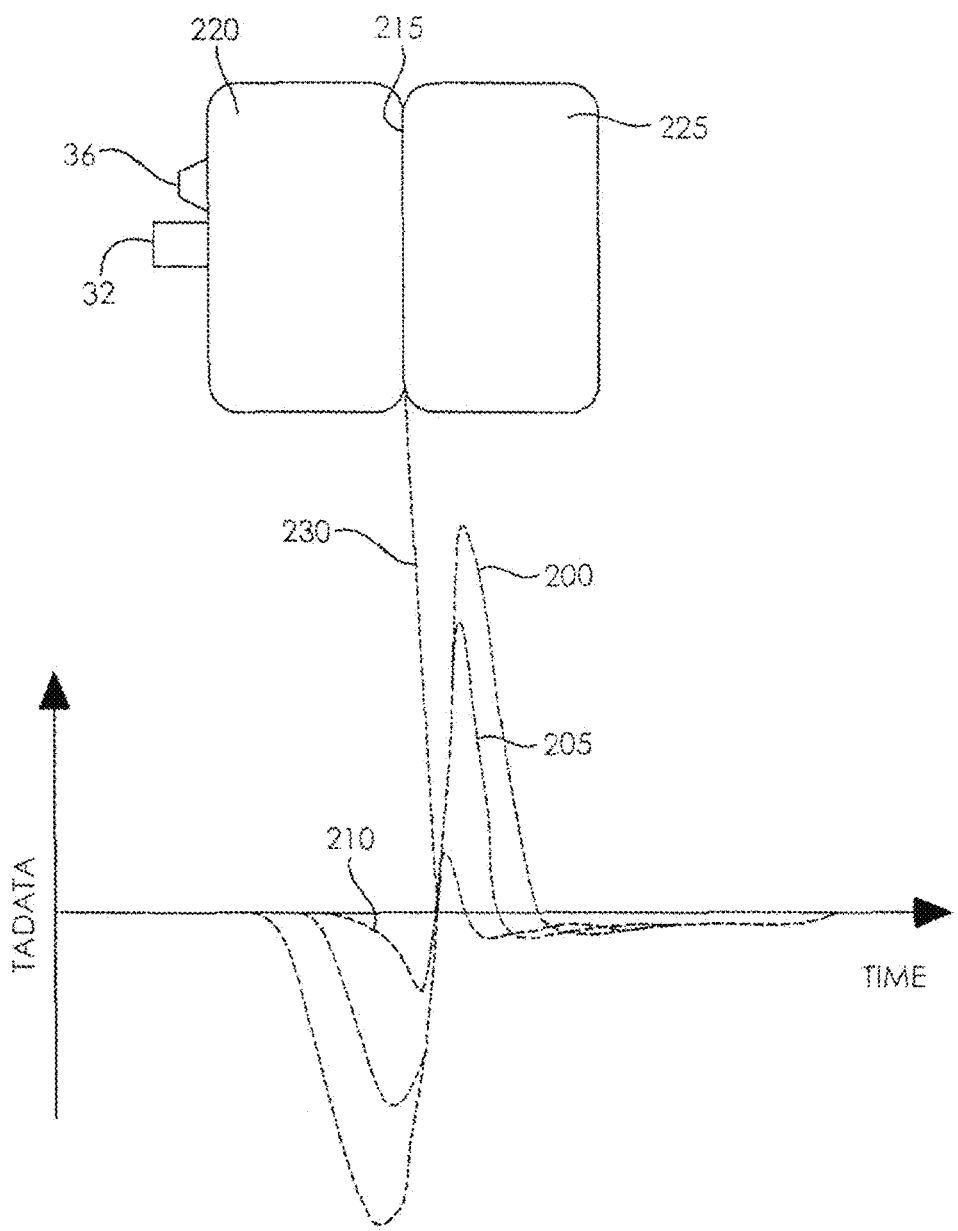
FIG. 2 is a graph showing exemplary multi-polar signals generated in response to thermoacoustic imaging of a tissue region of interest comprising different tissue materials separated by a boundary.

Exemplary multi-polar acoustic signals 200, 205 and 210 are shown in FIG. 2. In this example, the multi-polar acoustic signals 200, 205 and 210 are generated in response to thermoacoustic imaging of a tissue region of interest ROI comprising a first material 220 and a different type of second material 225 that are separated by a boundary 215. The dashed line 230 indicates a time point corresponding to the boundary 215. The differences in the peak-to-peak values of the multi-polar acoustic signals 200, 205 and 210 represent the extent to which the first material 220 expands into the boundary 215 and into the second material 225 before contracting. As the difference between the amount of energy absorbed of the two different materials at the boundary 215 increases, the amount that the first material 220 expands into the boundary 215 and into the second material 225 increases. As such, the peak-to-peak amplitude of each multi-polar acoustic signal 200, 205 and 210 is proportional to the difference between the amount of energy absorbed by the two materials 220, 225. As can be seen, the peak-to-peak value of multi-polar acoustic signal 200 is greater than that of multi-polar acoustic signals 205, 210 and the peak-to-peak value of multi-polar acoustic signal 205 is greater than that of multi-polar acoustic signal 210. As such, the difference between the amount of energy absorbed by the two materials 220, 225 when multi-polar acoustic signal 200 is generated is greater than the difference between the amount of energy absorbed by the two materials 220, 225 when multi-polar acoustic signal 205 is generated. Similarly, the difference between the amount of energy absorbed by the two materials 220, 225 when multi-polar acoustic signal 205 is generated is greater than the difference between the amount of energy absorbed by the two materials 220, 225 when multi-polar acoustic signal 210 is generated.

Figure 3:
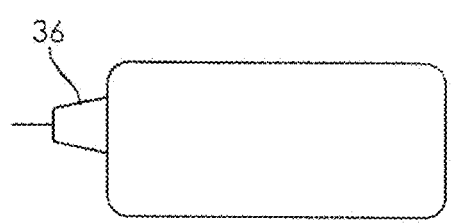
FIG. 3 is a graph showing exemplary electric field strength attenuation curves.
Figure 3:
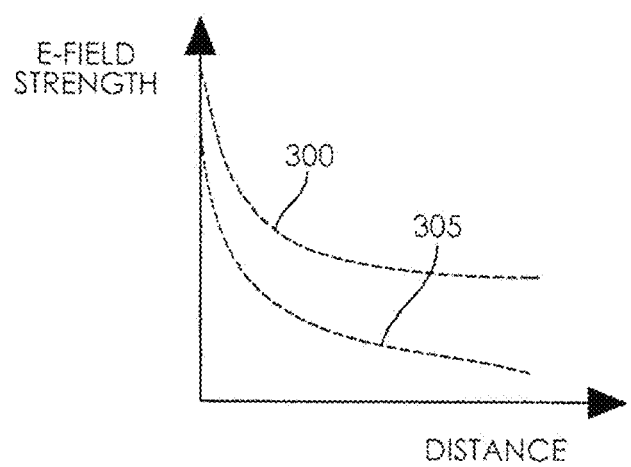

FIG. 3 shows electric field strength attenuation curves 300, 305 in material 310, 315 as a function of distance from the RF emitter 112 of a thermoacoustic imaging system. The example is simplified and ignores factors such as reflections off an object boundary. Each electric field strength attenuation curve 300, 305 represents the electric field strength attenuation of material 310, 315, respectively, as a function of distance from the RF applicator 36. Each electric field strength attenuation curve 300, 305 corresponds to a material, each of which has a different attenuation coefficient (which could correspond to a different fat concentration for each respective material). The material associated with electric field strength curve 300 has a lower attenuation coefficient than the material associated with electric field strength curve 305. In one embodiment, the material with a lower attenuation coefficient is has a high fat concentration (e.g. greater than 10%) and the material with a higher attenuation coefficient has a low fat concentration (e.g. less than 10%).

The material 310 associated with electric field strength attenuation curve 300 has a different Grüneisen parameter than the material 315 associated with electric field strength attenuation curve 305.

Different materials (e.g. tissues) have characteristic dielectric properties at a given frequency and a temperature. The dielectric properties of a material determines how much energy is absorbed by the material. An electric field transmitted through the material is attenuated, and the amount of attenuation is determined by both dielectric and physical properties of the material. As an example, compared to normal tissue, fatty tissue absorbs less energy and thus attenuates less electric field. Knowing these properties, the amount of attenuation through a material can be estimated. Furthermore, for a given RF applicator with specific design and tuning, dielectric properties of a material lead to different RF matching and energy delivery. For example, if the applicator is tuned to match well on human body, it is likely to match poorly to material with high water content, such as ultrasound gel. Therefore, knowing the RF power and matching properties gives information on the material in contact with the applicator.

Figure 4:
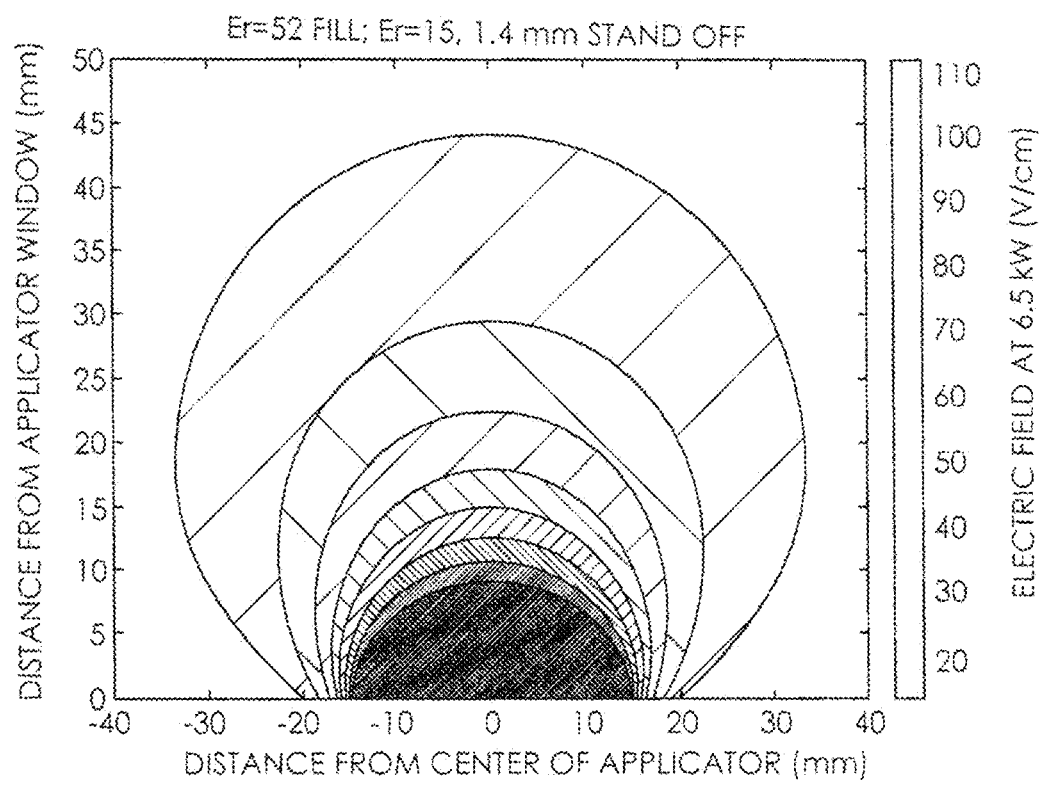
FIG. 4 is a graph showing exemplary flux (energy gradient) of RF energy pulses.

FIG. 4 shows the flux (energy gradient) of an RF energy pulse generated by the RF applicator 36. The RF applicator 36 is located and centered at the 0 value of the x-axis. As can be seen, as the distance from the center of the RF applicator 36 increases, the electric field strength decreases. In other embodiments, actual E-field distribution can have more complex shapes, depending on the modeled object.

Figure 5:
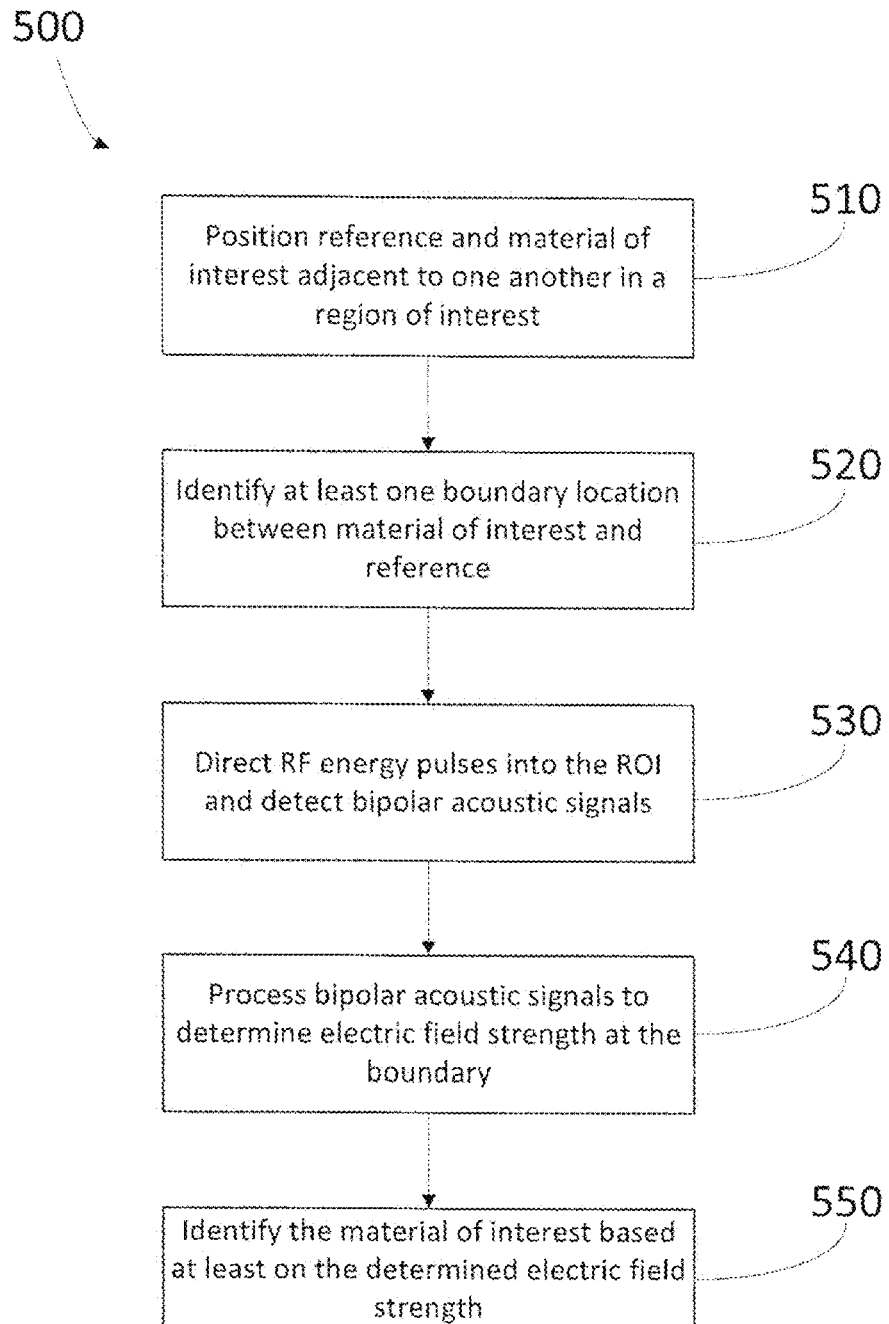
FIG. 5 is a flowchart of a method for determining at least one parameter of interest of a material.

Turning now to FIG. 5, a method for determining at least one parameter of interest of a material is shown and is generally identified by reference numeral 500. Initially during the method, a reference and a material having at least one parameter of interest are positioned adjacent to one another within a region of interest ROI (step 510). In this embodiment, the region of interest ROI is in vitro.

In an embodiment that is outside of a human body, the reference can be in the form of a pad and is made of a known material, such as for example rubber. Other examples of pad construction can include but are not limited to gels made of materials such as agar, gelatin, gelwax, or the like. The pad should have known dielectric properties, low acoustic attenuation properties, minimal RF interference properties, and good acoustic matching properties. The reference or pad is over top of the material of interest.

At the boundary 126 and 144, multi-polar acoustic signals are generated that are detected and received by the thermoacoustic transducer 32 (step 520).

The multi-polar acoustic signals received by thermoacoustic transducer 32 are communicated as thermoacoustic data to the computing device 22 for processing (step 530). In this embodiment, the computing device 22 is programmed to process the multi-polar acoustic signals to determine an electric field strength at the boundary.

The thermoacoustic pressure $p(\underline{r}, t)$ produced by a heat source $H(\underline{r}, t)$ obeys the following equation:

$$\nabla^2 p(\underline{r}, t) - \frac{1}{c^2} \frac{\partial^2}{\partial t^2} p(\underline{r}, T) = -\frac{\beta}{c_p} \frac{\partial}{\partial t} H(\underline{r}, T) \quad (1)$$

where $\underline{r}$ is the spatial position vector, $\beta$ is the isobaric volume expansion coefficient, c is the sound speed and $C_p$ is the specific heat capacity. Solving equation 1 with respect to the acoustic pressure wave $p(\underline{r}, t)$ yields the following forward problem:

$$p(\underline{r}, t) = \frac{\beta}{4\pi C_p} \iiint \frac{\partial \underline{r}}{|\underline{r} - \underline{r}'|} \frac{\partial H(\underline{r}', t')}{\partial t'} \bigg|_{t' = t - \frac{r'}{c}} \quad (2)$$

The heat source $H(\underline{r}, t)$ is modeled as the product of two factors, which are the spatial distribution of energy absorption $A(\underline{r})$ and the temporal irradiation function $I(t)$. The spatial distribution of energy absorption $A(\underline{r})$ is determined based on characteristics of the materials(s) being imaged. Since the thermoacoustic transducer array 30 has a finite bandwidth, received thermoacoustic data $p_d(\underline{r}, t)$ is a result of the convolution of acoustic pressure wave $p(\underline{r}, t)$ and the impulse response of the thermoacoustic transducer array 30 h(t) as set out in equation 3:

$$p_d(\underline{r}, t) = p(\underline{r}, t) *_t h(t) \quad (3)$$

where $*_t$ denotes a one-dimensional temporal convolution.

As will be appreciated, for conventional thermoacoustic imaging, the goal is to recover the spatial absorption distribution A(r) by inverting the forward problem. As such, the irradiation function is modeled as a temporal function that is uniform at a given time point.

Due to the limited bandwidth of the thermoacoustic transducer array 30, accurately recovering the absorption distribution is not trivial. As such, extracting quantitative information requires sophisticated methods beyond that of conventional reconstruction methods.

When the material having the parameter of interest is heated with a pulse of RF energy, the power deposition per unit volume $A(\underline{r})$ is expressed as:

$$A(\underline{r}) = \omega \varepsilon_0 \varepsilon''_r E^2(\underline{r}) \quad (4)$$

where $\omega$ is the radian frequency, $\varepsilon_0$ is the vacuum permittivity, $\varepsilon''_r$ is the imaginary part of the relative permittivity (also referred to as the conductivity) of the material having the parameter of interest and $E(\underline{r})$ is the electric field strength. The strength of thermoacoustic data $S(\underline{r})$ obtained from the material having the parameter of interest is the product of the deposited energy and the Grüneisen parameter of the tissue $\Gamma$:

$$S(\underline{r}) = \Gamma A(\underline{r}) = \Gamma \omega \varepsilon_0 \varepsilon''_r E^2(\underline{r}) \quad (5)$$

Within a dielectric lossy medium, the electric field strength is attenuated as it propagates through the medium. The amount of attenuation is determined by various factors such as for example characteristics of region of interest and characteristics of the RF applicator 36. The spatial distribution of the electric field is:

$$E(\underline{r}) = E_0 E_A(\underline{r}) \quad (6)$$

where $E_0$ is the maximum electric field strength of the region of interest and $E_A(r)$ is the attenuation of the electric field over a given space. For a simple 1D case, the attenuation $E_A(\underline{r})$ can be expressed in exponential form:

$$E_A(d) = e^{-\eta d} \quad (7)$$

where $\eta$ is the electric field absorption coefficient of the region of interest and d is the distance of the region of interest from the RF applicator 36.

In this embodiment, equation 5 is used as a model to infer material parameters from the thermoacoustic data. As mentioned, thermoacoustic data obtained from the region of interest is in the form of multi-polar acoustic signals. The strength or peak-to-peak amplitudes of the multi-polar acoustic signals represent the absorption property difference between the material having the parameter of interest and the reference. Further, the phase of the thermoacoustic data at the boundary indicates which material (the material having the parameter of interest or the reference) has a higher or lower absorption coefficient. The strength or peak-to-peak amplitudes $S_I$ of each multi-polar acoustic signal measured at the boundary location, r, is expressed in equation 8:

$$S_I = (\Gamma_{MOI} \varepsilon''_{r,MOI} - \Gamma_{ref} \varepsilon''_{r,ref}) \omega \varepsilon_0 E_I^2 \quad (8)$$

where MOI denotes the material having the parameter of interest, ref denotes the reference, and $E_I$ denotes the incident electric field strength at the boundary.

As shown in equation 8, the strength of the multi-polar acoustic signal is determined by material parameters and the strength of the electric field at the boundary.

Using equation 6, the incident electric field $E_I$ at a boundary location (going from the reference to the material having the parameter of interest) can be estimated as:

$$E_I = E_0 e^{-n_{ref} d_{ref}} \qquad (9)$$

where $E_0$ is the electric field strength at the start of the reference, $\eta_{ref}$ is the attenuation coefficient of the reference, and $d_{ref}$ is a thickness of the reference. As will be appreciated, the electric field strength $E_0$ may be modeled using a finite-difference time domain (FDTD method) or may be inferred from measurements taken at the RF applicator 36. The electric field strength $E_0$ may alternatively be directly measured at the boundary using an electric field probe.

The multi-polar acoustic signal strength at a boundary location can be derived from equations 8 and 9:

$$S_I = (\Gamma_{MOI} \varepsilon''_{r,MOI} - \Gamma_{ref} \varepsilon''_{r,ref}) \omega \varepsilon_0 E_I^2 \qquad (10)$$

$$= (\Gamma_{MOI} \varepsilon''_{r,MOI} - \Gamma_{ref} \varepsilon''_{r,ref}) \omega \varepsilon_0 \left( E_0 e^{-n_{ref} d_{ref}} \right)^2$$

Equation 10 can be deduced to:

$$\Gamma_{MOI} \varepsilon''_{r,MOI} = \frac{S_I}{\omega \varepsilon_0 \left( E_0 e^{-n_{ref} d_{ref}} \right)^2} + \Gamma_{ref} \varepsilon_0 \varepsilon''_{r,ref} \qquad (11.1)$$

Radio frequency (RF) characteristics are used to determine the parameter of interest of the material. In this embodiment, a Voltage Standing Wave Ratio (VSWR) is calculated (step 540) and is a measure of how efficiently RF power is being transmitted from the RF applicator. Generally, the VSWR is calculated by monitoring the RF forward and reflected power of the RF energy pulses. The RF forward power is the power of the RF energy pulses emitted by the RF applicator. The RF reflected power is the power of the RF energy pulses that are reflected back to the RF applicator. Using the RF forward and reflected powers, the voltage standing wave ratio (VSWR) is calculated.

As mentioned previously, during step 520, RF energy pulses are directed into the region of interest that comprises the material having the parameter of interest. The RF energy pulses have a known frequency and a known amplitude. In this embodiment, a first power monitor is used to measure the forward power of the RF energy pulses. A second power monitor is used to measure the reflected power of the RF energy pulses.

The VSWR is calculated as a ratio of the measured forward power and the measured reflected power.

In one example, a user analyzes a liver tissue sample with unknown fat content. If the reference layer is not too thick, the property of that liver would affect the matching of the applicator to the object (reference/liver tissue). The VSWR value of the sample may not be sensitive enough to determine what the fat content of the liver is. However, the VSWR value can be widely different from having a different object under the reference. VSWR can be affected by both the identity of the object and its property. It may not be the dominating factor in the decision regarding an object, but knowledge of the VSWR still has value.

At least one parameter of interest of the material is determined using the determined electric field strength and the calculated VSWR (step 550). In this embodiment, the parameter of interest of the material may be at least one of conductivity ($\varepsilon''_r$) (S/m), Grüneisen parameter ($\Gamma$), specific heat capacity ($\Gamma$) and/or a parameter $k_{MOI}$.

The conductivity ($\varepsilon''_r$) of the material may be calculated using thermoacoustic signal strength and the Gruneisen parameter ($\Gamma$).

The Gruneisen parameter ($\Gamma$) of the material may be calculated using the thermoacoustic signal strength and the conductivity ($\varepsilon''_r$) of the material.

Specific heat capacity ($\gamma$) is calculated using known equations, such as the one shown below as equation 12.

$$\gamma = \frac{\alpha K_T}{\rho C_V} = \frac{\alpha K_S}{\rho C_P} = \frac{\alpha v_s^2}{C_P} \qquad (12)$$

where $C_p$ and $C_v$ are the principal (i.e. per-mass) heat capacities at constant pressure and volume, a is the volume thermal expansion coefficient, $K_S$ and $K_T$ are the adiabatic and isothermal bulk moduli, $v_s$ is the speed of sound in the medium, and p is density.

The parameter $k_{MOI}$ represents how much thermoacoustic signal will be generated for a given amount of energy. It is the multiplication of (energy absorption) and (absorbed energy conversion to acoustic signal). The parameter $k_{MOI}$ is calculated by solving the following equation:

$$k_{MOI} = \Gamma_{MOI} \varepsilon''_{r,MOI} = \frac{S_I}{\omega \varepsilon_0 \left( E_0 e^{-n_{ref} d_{ref}} \right)^2} + \Gamma_{ref} \varepsilon_0 \varepsilon''_{r,ref} \qquad (11.2)$$

Table 1 summarizes the measurements required to determine a particular parameter of interest:

TABLE 1

Lookup Table to Determine Parameter of Interest of an Unknown Material

| Parameter to be determined | Required Measurements | Relevant equation |
|---|---|---|
| Conductivity ($\varepsilon_r''$) (S/m) | Thermoacoustic signal strength Grüneisen parameter ($\Gamma$) | 11.1 |
| Grüneisen parameter ($\Gamma$) | Thermoacoustic signal strength Conductivity ($\varepsilon_r''$) | 11.1 |
| Specific heat capacity ($\gamma$) | Thermoacoustic signal strength conductivity ($\varepsilon_r''$) speed of sound volume thermal expansion coefficient adiabatic or isothermal bulk moduli density mass | 12 |
| Parameter $k_{MOI}$ | conductivity ($\varepsilon_r''$) Grüneisen parameter ($\Gamma$) | 11.2 |

Although during method 500 the identity of the material having the parameter of interest is known, at least one parameter of interest may be determined if the identity of the material is unknown. In this embodiment, Table 2 is used to determine at least one parameter of interest of an unknown material:

TABLE 2

Lookup Table to Determine Parameter of Interest of an Unknown Material

| | Measurements | | Material at condition 1 | Material at condition 2 |
|---|---|---|---|---|
| Quantitative | Thermoacoustic | Material independent characteristic TA signal<br>Corrected TA signal at the reference to material boundary<br>Characteristic TA property (Grüneisen × Conductivity) | | |
| | Power measurements (no reference) | Forward<br>Transmitted<br>VSWR | | |
| | Power measurements (with reference) | Forward<br>Transmitted<br>VSWR | | |
| | Combined metrics | Ratio between TA signals<br>Function of ratio between TA signals and TA properties<br>Function of TA signal, properties, and power measurements | | |
| | Ultrasound | Speed of sound | | |
| Semi-quantitative | Ultrasound | Scattering | | |
| Other characteristics | Color<br>Transparency<br>Texture<br>Material state<br>Odor | | | |

Experiments and/or modeling will be utilized to generate the data for Table 2 at selected condition(s). For a material with unknown property, various measurements can be made at different condition(s) and compared against the lookup table. Then, a parameter can be determined at the different condition(s) by estimating the effect that the change in condition(s) (selected condition(s) versus different condition(s)) has upon the parameter.

Semi-quantitative measurements may be used to help determine the parameter of interest. For example, for a material with an unknown condition, each quantitative property (e.g. parameter of interest) may be compared against conditions listed in Table 2. An exemplary comparison metric is shown in equation 13:

$$Q_i = \Sigma_{j=1}^{N} (p^j_i - p^j_{unknown}) w^j \quad (13)$$

where N is the total number of quantitative property being included in the comparison, i denotes the $i^{th}$ condition in the lookup table, j denotes $j^{th}$ material property, $p^j_i$ denotes the $j^{th}$ property of material with $i^{th}$ condition $p^j_{unknown}$ denotes the $j^{th}$ property of the material with unknown condition, $w^j$ denotes a weighting factor for $j^{th}$ property. Material with the lowest $Q_i$ will be considered as the identified condition of the material. As will be appreciated, only part of the materials properties may be used to determine the material condition.

In some embodiments, the identity of the material will not be directly selected from the lookup table, but the likelihood of its identity will be suggested based on the acquired metrics. For example, a material may have 60% likelihood to be material 1 and 40% likelihood to be material 2.

Those skilled in the art will appreciate that the at least one parameter of interest may be used to help identify the material using a lookup table generated from previously performed models and experiments. Table 3 illustrates an exemplary lookup table:

TABLE 3

Grüneisen Parameter and Conductivity of Materials at Room Temperature (at 434 MHz)

| | Distilled Water | Subcutaneous fat | Muscle | Blood | Mineral Oil |
|---|---|---|---|---|---|
| Grüneisen parameter (Γ) | 0.11 | 0.81 | 0.21 | 0.14 | 0.71 |
| Conductivity ($\varepsilon_r''$) (S/m) | 0.045 | 0.042 | 0.8 | 1.36 | 0 |
| Parameter (k) | 0.00495 | 0.03402 | 0.168 | 0.1904 | 0 |

Those skilled in the art will appreciate that other parameters of interest of the material may be determined. For example, a lookup table comprising physical characteristics of the material may be used. Table 4 illustrates an exemplary lookup table:

TABLE 4

Physical Characteristics of Materials

| | Distilled water | Fat | Mineral oil | Concrete |
|---|---|---|---|---|
| Color | colorless | white | colorless | white/gray/colored |
| Transparency | transparent | opaque | transparent | opaque |
| Odor | odorless | rancid | odorless | concrete odor |
| texture | smooth | smooth | smooth | rough |
| material state | liquid | solid | liquid | solid |

Those skilled in the art will appreciate that the ultrasound imaging system may be used to determine at least one parameter of interest of the material. For example, the speed of sound and scattering properties of the material can be observed and compared to the speed of sound and scattering properties of the reference. The ultrasound imaging system may also be used to inspect a condition of the material and to check for undesirable structures such as for example cracks or air bubbles that may interfere with the thermoacoustic imaging process.

Those skilled in the art will appreciate that the phase of the multi-polar acoustic signals may be used to help identify at least one parameter of interest of the material. Since the reference is made of a known material, the material that absorbs more energy than the other material expands rapidly across the boundary and into the other material, that expands less, and then quickly contract. The phase of the multi-polar acoustic signal depends on which one of the materials absorbs more energy.

Those skilled in the art will appreciate that the strength or peak-to-peak values of the multi-polar acoustic signals may be used to help identify at least one parameter of interest of the material. Since the reference is made of a known material with a known absorption property and the strength or peak-to-peak values of the multi-polar acoustic signals depend on the relative absorption properties of the materials, the absorption property of the material can be deduced.

Although the reference is described as being in the form of a pad made of a known material and is placed on top of the material, those skilled in the art will appreciate that alternatives are available. For example, in another embodiment the reference may be in the form of a container or petri dish configured to hold or contain the material of interest.

In one embodiment, the pad is flexible. For example, the pad can be flexible enough to provide good contact with a cylindrical object.

Figure 6:
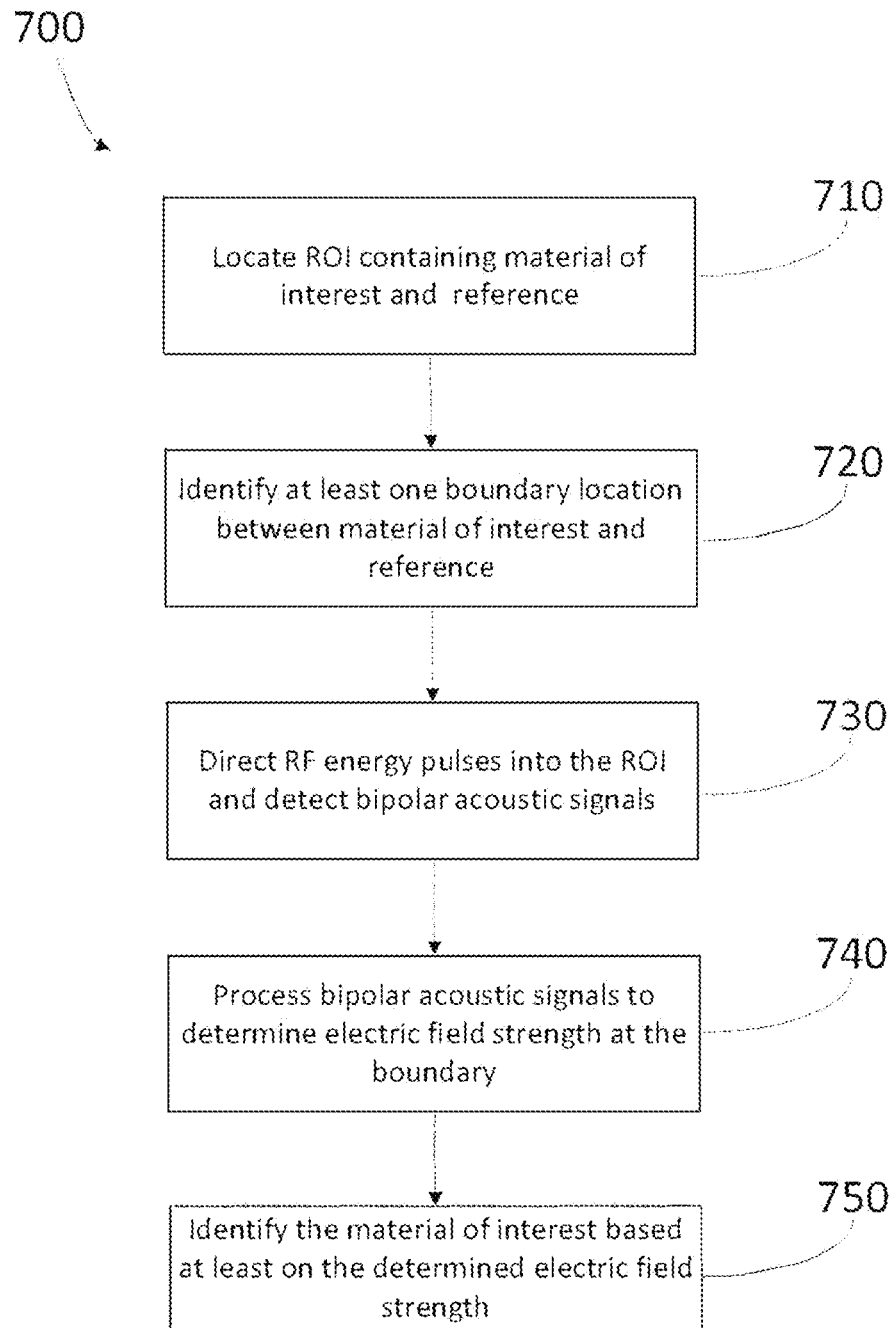
FIG. 6 is a flowchart of another method determining at least one parameter of interest of a material.
Figure 7:
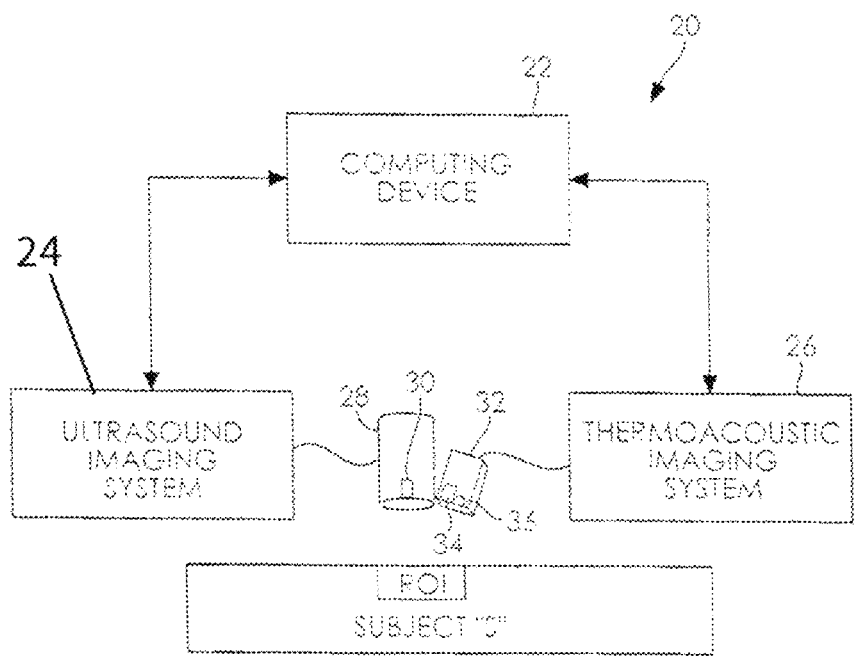
FIG. 7 is a schematic view of the imaging system wherein the region of interest is in vivo.

Turning now to FIG. 6, another embodiment of a method for identifying a material of interest is shown and is generally identified by reference numeral 700. Method 700 is generally identical to that of method 500 with the following exceptions. During method 700, rather than the region of interest being in vitro, in method 700 region of interest is in vivo. As such, initially during the method, a region of interest ROI that contains a material having a parameter of interest and a reference are located within a subject's body (step 510). In this embodiment, the region of interest ROI is located using the ultrasound imaging system 24. Specifically, ultrasound image data obtained by the ultrasound imaging system 24 is communicated to the computing device 22. The ultrasound image data is processed by the computing device 22 and a reconstructed ultrasound image is presented on the display device. The operator moves the ultrasound transducer 28 until the region of interest is located. When locating the region of interest, the computing device 22 overlays information associated with the angle of the centerline of the one or more transducer arrays 30 of the ultrasound transducer 28 overtop of the reconstructed ultrasound image on the display device. The information is used to provide feedback to the operator to ensure the axial axis of the ultrasound transducer 28 is generally perpendicular to a boundary between the material and the reference.

Once the region of interest ROI has been located, at least one boundary between the material having the parameter of interest and the reference is identified (step 715). In this embodiment, one boundary location is identified and this is done using ultrasound images generated by the ultrasound imaging system. The boundary location is identified by the operator using an input device such as a mouse coupled to the computing device 22.

Once the boundary has been identified, steps 720, 730, 740 and 750 of method 700 are generally identical to that of steps 520, 530, 540 and 550 of method 500, respectively.

Those skilled in the art will appreciate that in some embodiments the thermoacoustic data may need to be corrected. For example, the shape of the boundary may be deformed. In this embodiment, the shape and/or angle of the boundary may be estimated using the ultrasound imaging system and known image processing techniques.

In this embodiment, received signals at the thermoacoustic transducer array may be expressed using equation 14:

$$p_s(t) = \int_S p(\underline{r}, t) dS \qquad (14)$$

where S is the surface area of the thermoacoustic transducer array. As will be appreciated, the properties of the thermoacoustic transducer array and its positioning relative to the region of interest change the characteristics of the thermoacoustic data. The multi-polar acoustic signals received by the thermoacoustic transducer array are affected by various factors that are not related to signal generation by rather associated with signal propagation. These factors depend on transducer spatial sensitivity, relative positioning between the thermoacoustic transducer array and the boundary between the material and the reference, and the relative shape of the reference with respect to the thermoacoustic transducer array surface. Even for the same region of interest and the same thermoacoustic transducer array, changing the position and angle of the thermoacoustic transducer array during thermoacoustic data acquisition results in different measurements.

In this embodiment, a compensation factor is calculated based on information and measurements provided by the operator or estimated using acquired ultrasound image data. The compensation factor may be a single factor or multiple factors, where each factor is calculated information such as size and shape of the reference and the angle between the ultrasound transducer array and the boundary. In one embodiment, the compensation factors are calculated based on theoretical methods such as by using acoustic propagation and ultrasound transducer properties. In another embodiment, the compensation factors may be obtained from phantom and clinical studies. In yet another embodiment, both theoretical and experimental methods may be used.

When the thermoacoustic data is adjusted with the compensator factor, the thermoacoustic signal strength, $S_l$, in equation 12 is replaced by the adjusted thermoacoustic signal strength, $S_j$:

$$k_{MOI} = \Gamma_{MOI} \varepsilon''_{r,MOI} = \frac{S_l}{\omega \varepsilon_0 \left(E_0 e^{-n_{ref} d_{ref}}\right)^2} + \Gamma_{ref} \varepsilon_0 \varepsilon''_{r,ref} \qquad (15)$$

In this, when the material having the parameter of interest is large enough to ignore the partial volume effect, only the angle based adjustment is required. When a tangent vector of the material at the boundary and the centerline of the one or more transducer arrays 34 is not perpendicular, signal adjustment is made to the acquired measurement. This adjustment is expressed as:

$$S_j = S_l C(\theta) \qquad (16)$$

where C is an angle based adjustment factor, θ is the angle between the tangent vector of the material at the boundary and the centerline of the one or more transducer arrays 34.

In some embodiments, various measurements from thermoacoustic data can be used to construct a parameter, which may be tabulated and used to help identify the material. For example, thermoacoustic data having no object related signals may be obtained at the beginning of the measurements. For example, thermoacoustic data may be obtained with the coupling medium (e.g., ultrasound gel) being present, thermoacoustic data may be obtained and may comprise signals generated from internal components or transducer components, the boundary between the reference and the RF applicator, the internal components of the RF applicator, or other parts of the RF applicator. Thermoacoustic data from such sources are independent of the material and can be used to compensate or normalize the thermoacoustic signal from the material. A simple ratio between thermoacoustic data obtained at the reference to the boundary and thermoacoustic data having no object related signals may be used as a metric. As will be appreciated, various combinations of thermoacoustic data having no object related signals may be obtained.

Those skilled in the art will appreciate that in embodiments, the boundary between the reference and the material may be automatically defined using algorithms based on ultrasound segmentation or thermoacoustic data analysis. As will be appreciated, both operator-defined and automatic methods may be combined.

Figure 8:
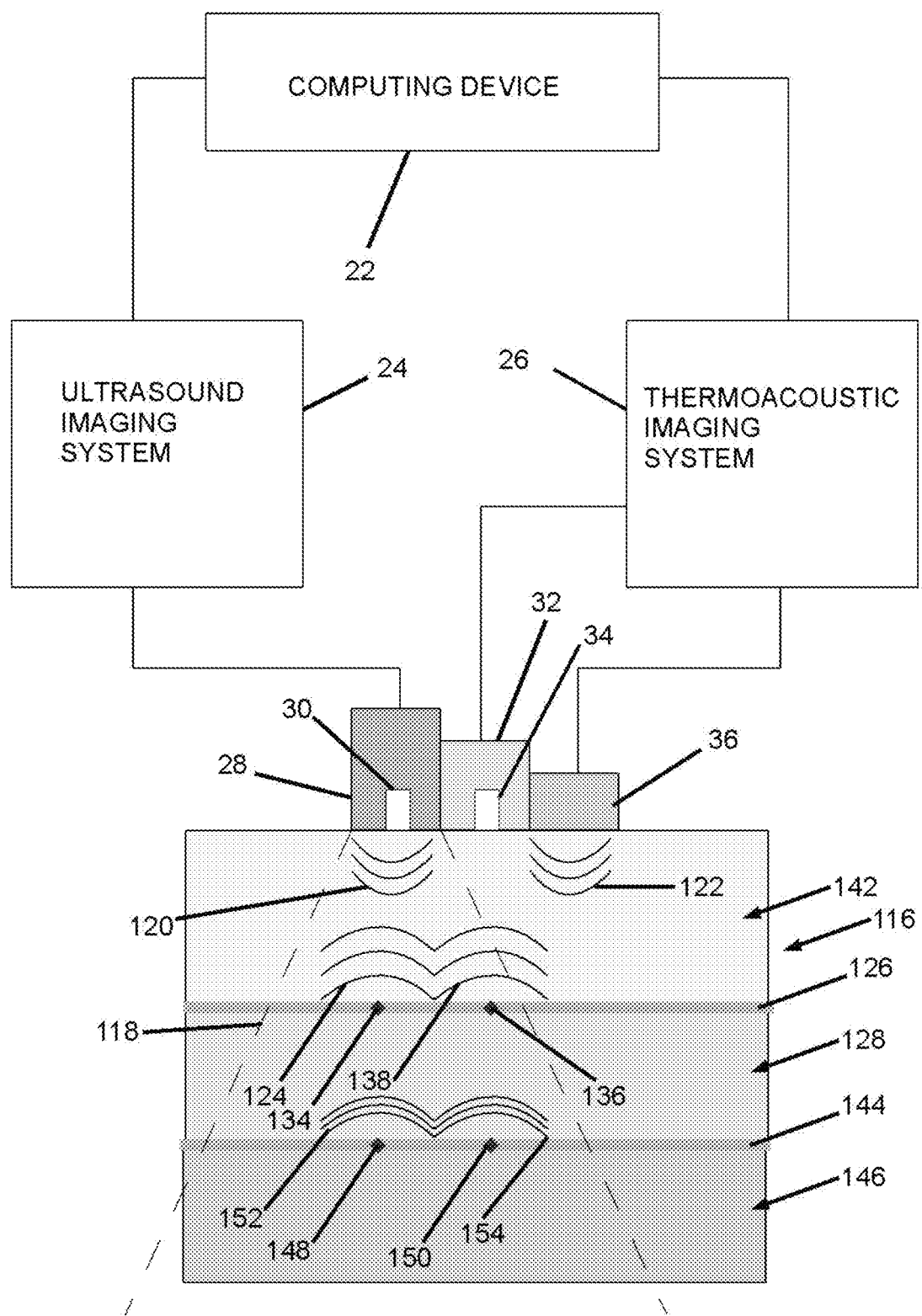
FIG. 8 is a schematic view of another embodiment of an imaging system.

Although in embodiments a single boundary, a single material and a single reference are imaged, those skilled in the art will appreciate that alternatives are available. An example is shown in FIG. 8. In this embodiment, a user utilizes the computing device 22 to operate the ultrasound imaging system 24. The ultrasound imaging system 24 sends a signal to the one or more ultrasound transducer arrays 30, which sends sound waves 120 into reference 142 which is in the form of a pad made of a known material and is positioned within the region of interest 116. Within the region of interest 116, there is a first boundary 126 at first boundary locations 134 and 136, a first material 128, a second material 146, and a second boundary 144 at second boundary locations 148 and 150. The ultrasound transducer arrays 30 receive reflected sound waves to generate a B-mode image via the ultrasound imaging system 24. The extent of the B-mode image is conical in shape and is shown with B-mode image limits 118. The B-mode image gives the physical location of boundary 126, enabling the computing device 22 to correlate obtained data from the thermoacoustic transducer array 34 and RF emitter 36. Once position coordinates are known, the ultrasound imaging system 24 is turned off to eliminate potential interference with the thermoacoustic imaging system 26. The thermoacoustic imaging system then initiates the RF emitter 36 to send RF energy pulses 122 into reference 142. The RF energy 122 pulses are absorbed in the region of interest 116. The difference between RF energy absorbed in the reference 142 and the first material 128 creates multi-polar acoustic signals 124 and 138 emanating from boundary locations 134 and 136. In addition, the difference between RF energy absorbed in the first material 128 and the second material 146 creates multi-polar acoustic signals 152 and 154 emanating from boundary locations 148 and 150. The known parameters of the reference 142 can then be used in conjunction with thermoacoustic data from the multi-polar acoustic signals generated at boundary locations 134 and 136 to determine at least one parameter of the first material 128. Additionally, the at least one parameter of interest of the first material 128 can be used in conjunction with thermoacoustic data from the multi-polar acoustic signals generated at boundary locations 148 and 150 to determine at least one parameter of interest of the second material 146.

Although in embodiments described above the one or more ultrasound transducer arrays are described as being disconnectable from the ultrasound imaging system and reconnectable to the thermoacoustic imaging system, those skilled in the art will appreciate that alternatives are available. For example, the one or more ultrasound transducer arrays may be connected to a hub which itself is connected to the ultrasound imaging system and the thermoacoustic imaging system. In this embodiment, the hub may be controlled by the computing device or by other input to switch operation between the ultrasound imaging system and the thermoacoustic imaging system and vice versa.

Although in embodiments described above a metric used to estimate the signal strength at the boundary is the difference between two or more peaks of a multipolar signal, those skilled in the art will appreciate that the metric may be a simple peak (maximum), a p-norm, area under the multipolar signal, etc.

As will be appreciated, embodiments of image processing described above can be performed on ultrasound and thermoacoustic images in real-time or off-line using images stored in memory.

Although the thermoacoustic imaging system is described as comprising an RF applicator configured to generate short pulses of RF electromagnetic radiation, those skilled in the art will appreciate that in other embodiments the thermoacoustic imaging system may comprise a visible light source or an infrared radiation source with a wavelength between 400 nm and 10 μm and a pulse duration between 10 picoseconds and 10 microseconds.

Although in embodiments described above the thermoacoustic imaging system and the ultrasound imaging system are described as using one or more ultrasound transducer arrays, those skilled in the art will appreciate that the alternatives are available. For example, a single transducer element, an ultrasound transducer array having a linear or curved one-dimensional array, or a two-dimensional ultrasound transducer array may be used.

Although in embodiments described above, thermoacoustic data is obtained of a single region of interest, those skilled in the art will appreciate that multiple regions of interest may be analyzed and combined.

Those skilled in the art will appreciate that the above-described ultrasound image data and thermoacoustic data may be one-dimensional, two-dimensional or three-dimensional. In embodiments, the ultrasound image data may be in a different dimension than the thermoacoustic data. For example, ultrasound image data may be two-dimensional and the thermoacoustic data may be one-dimensional. Further, different fields of view may be used.

In another embodiment, different types or models of transducer arrays may be used with the thermoacoustic and ultrasound imaging systems. In this embodiment, a transform may be used to map a thermoacoustic absorption data to the ultrasound image. In another embodiment, in the event that knowledge of transducer array geometry is not readily available, the thermoacoustic absorption data may be mapped to the ultrasound image using a phantom with reference points. In this embodiment, a transform may be used to map known phantom reference points from the thermoacoustic absorption data to the phantom reference points on the ultrasound image.

Although the ultrasound imaging system is described as using B-mode ultrasound imaging techniques, other techniques may be used such as for example power Doppler images, continuous wave Doppler images, strain imaging, etc.

Although in embodiments described above thermoacoustic data is obtained of the region of interest, those skilled in the art will appreciate that thermoacoustic data may be obtained for an area larger than the region of interest.

As described above, the programmed computing device executes computer program code stored on at least one computer readable medium. The computer readable medium may be memory devices or transmitting devices, thereby making a computer program product or article of manufacture according to the invention. As such, functionality may be imparted on a physical device as a computer program existent as instructions on any computer-readable medium such as on any memory device or in any transmitting device, that are to be executed by a processor.

Examples of memory devices include, hard disk drives, diskettes, optical disks, magnetic tape, semiconductor memories such as FLASH, RAM, ROM, PROMS, and the like. Examples of networks include, but are not limited to, the Internet, intranets, telephone/modem-based network communication, hard-wired/cabled communication network, cellular communication, radio wave communication, satellite communication, and other stationary or mobile network systems/communication links.

A machine embodying the invention may additionally or alternatively include one or more processing systems including, for example, computer processing unit (CPU) or processor, memory/storage devices, communication links, communication/transmitting devices, servers, I/O devices, or any subcomponents or individual parts of one or more processing systems, including software, firmware, hardware, or any combination or subcombination thereof.

Using the description provided herein, embodiments described above may be implemented as a machine, process, or article of manufacture by using standard programming and/or engineering techniques to produce programming software, firmware, hardware or any combination thereof.

Using the description provided herein, those skilled in the art will be readily able to combine software created as described with appropriate or special purpose computer hardware to create a computer system and/or computer subcomponents embodying the invention, and to create a computer system and/or computer subcomponents for carrying out at least some steps of the methods described herein.

Those skilled in the art will appreciate that in embodiments the computing device may be programmed to adjust parameters of the RF applicator.

Those skilled in the art will appreciate that the above-described method may be performed on a phantom designed to mimic an area of interest. In this embodiment, the RF applicator may be adjusted to maximize the peak-to-peak amplitudes of the multi-polar acoustic signals prior to imaging a material. Further, the method may be performed on numerous phantoms of various properties to mimic different materials.

Although embodiments have been described above with reference to the accompanying drawings, those of skill in the art will appreciate that variations and modifications may be made without departing from the scope thereof as defined by the appended claims.

What is claimed is:

1. A method for determining at least one parameter of interest of a material, the method comprising:
    directing, using a radio frequency (RF) applicator, one or more RF energy pulses into a region of interest, the region of interest comprising a material having a parameter of interest and at least one reference, the material and the reference separated by at least one boundary;
    detecting, using an acoustic receiver, at least one multi-polar acoustic signal generated in the region of interest in response to the RF energy pulses;
    processing the at least one multi-polar acoustic signal to determine an electric field strength at the boundary;
    calculating a voltage standing wave ratio (VSWR) of the one or more RF energy pulses;
    monitoring a forward power and a reflected power of the one or more RF energy pulses to calculate the VSWR, and
    determining the at least one parameter of interest of the material based at least on the determined electric field strength and the VSWR.

2. The method of claim 1 wherein the at least one parameter of interest is one of a Gruneisen Parameter of the material and a conductivity of the material.

3. The method of claim 2, wherein the at least one parameter of interest is a product of the Gruneisen Parameter of the material and the conductivity of the material.

4. The method of claim 2 wherein the at least one parameter of interest is a specific heat capacity of the material.

5. The method of claim 1, wherein an identity of the material is known.

6. The method of claim 5, wherein the determining comprises estimating the at least on parameter of interest.

7. The method of claim 1, wherein an identity of the material is unknown.

8. The method of claim 7, wherein the determining comprises looking up the at least one parameter of interest in a lookup table.

9. The method of claim 1, wherein the electric field strength is determined based on an input power of the RF applicator and an attenuation coefficient of the reference.

10. The method of claim 1, wherein the electric field strength is determined based on an estimated thickness of the reference and an attenuation coefficient of the reference.

11. The method of claim 1 wherein each multi-polar acoustic signal corresponds to a separate boundary location.

12. The method of claim 1, wherein detecting the at least one multi-polar acoustic signal is achieved using a thermoacoustic imaging system.

13. A system for determining at least one parameter of interest of a material, the system comprising:
    a thermoacoustic imaging system comprising a radio frequency (RF) applicator configured to emit RF energy pulses into the region of interest comprising a material having at least one parameter of interest and a reference, the material and the reference separated by at least one boundary, and an acoustic receiver configured to receive at least one multipolar acoustic signal generated in the region of interest in response to the RF energy pulses; and
    one or more processors configured to:
    process multi-polar acoustic signals received by the acoustic receiver to determine an electric field strength at the boundary;
    calculate a voltage standing wave ratio (VSWR) of the one or more RF energy pulses;
    monitor a forward power and a reflected power of the one or more RF energy pulses to calculate the VSWR, and
    determine the at least one parameter of interest of the material based at least on the determined electric field strength and the VSWR.

14. The system of claim 13 wherein the at least one parameter of interest is one of a Gruneisen Parameter of the material and a conductivity of the material.

15. The system of claim 14 wherein the at least one parameter of interest is a product of the Gruneisen Parameter of the material and the conductivity of the material.

16. The system of claim 14 wherein the at least one parameter of interest is a specific heat capacity of the material.

17. The system of claim 13 further comprising at least one power monitor configured to monitor a forward and reflected power of the RF energy pulses, and the one or more processors are configured to calculate the VSWR using the forward and reflected power of the RF energy pulses.

18. The system of claim 13 wherein the electric field strength is determined based on an input power of the RF applicator and an attenuation coefficient of the reference.

19. A non-transitory computer readable medium having stored thereon computer program code executable by one or more processors to:

process at least one multi-polar acoustic signal generated in a region of interest comprising a material having a parameter of interest and at least one reference, the material and the at least one reference separated by at least one boundary, to determine an electric field strength at the boundary;

calculate a Voltage Standing Wave Ratio (VSWR) of RF energy pulses directed into the region of interest;

monitor a forward power and a reflected power of the one or more RF energy pulses to calculate the VSWR, and determine at least one parameter of interest of the material based at least on the determined electric field strength and the VSWR.

* * * * *